(12) United States Patent
Hunt et al.

(10) Patent No.: US 6,585,661 B1
(45) Date of Patent: Jul. 1, 2003

(54) DEVICE AND METHOD FOR MONITORING ASTHMA

(75) Inventors: John F. Hunt, Charlottesville, VA (US); Benjamin M. Gaston, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/857,820

(22) PCT Filed: Dec. 17, 1999

(86) PCT No.: PCT/US99/30184

§ 371 (c)(1),
(2), (4) Date: Jun. 11, 2001

(87) PCT Pub. No.: WO00/35337

PCT Pub. Date: Jun. 22, 2000

Related U.S. Application Data

(60) Provisional application No. 60/112,868, filed on Dec. 18, 1998.

(51) Int. Cl.[7] ................................................. A61B 5/08
(52) U.S. Cl. ..................................................... 600/532
(58) Field of Search ................................. 600/529–544

(56) References Cited

U.S. PATENT DOCUMENTS

| | | |
|---|---|---|
| 5,081,871 A | 1/1992 | Glaser |
| 5,922,610 A | 7/1999 | Alving et al. |
| 6,010,459 A | 1/2000 | Silkoff et al. |
| 6,033,368 A | 3/2000 | Gaston et al. |
| 6,135,107 A | 10/2000 | Mault |
| 6,148,657 A | 11/2000 | Satoh et al. |
| 6,190,326 B1 | 2/2001 | McKinnon et al. |
| 6,190,858 B1 | 2/2001 | Persaud et al. |
| 6,221,026 B1 | 4/2001 | Phillips |

FOREIGN PATENT DOCUMENTS

| | | |
|---|---|---|
| DE | 19505504 | 11/1995 |
| WO | WO97/35519 | 10/1997 |

OTHER PUBLICATIONS

Baldwin, et al, "Oxidant activity in expired breath of patients with adult respiratory distress", Lancet Journal, vol. 1, issue 8471, pp. 11–14.

Wilson, et al, "General anesthesia and exhaled breath hydrogen peroxide", Anesthesiology Journal, vol. 76, issue 5, pp. 703–710.

Blue Cross Blue Shield Billing Guideline: 44, Reviewed 5/99, "pH Monitoring and Urea Breath Testing".

American Standard Companies, download from Internet at www.americanstandard.com/annua197/medical.htm.

*Primary Examiner*—Max F. Hindenburg
*Assistant Examiner*—Pamela L. Wingood
(74) *Attorney, Agent, or Firm*—Robert J. Decker (57) ABSTRACT

A device (10) and method for non-invasively monitoring asthma and other respiratory diseases. The method includes collecting condensate from a subject's breath, testing the condensate to determine its acidity level or ammonium concentration, and evaluating these properties to determine the presence, absence or status of a respiratory disease in the subject. The method may also include, prior to the testing step, standardizing the volatile substances that may be present within the condensate in a degassing or gas standardizing step. The device (10) includes a mouthpiece apparatus (20) configured to receive breath from a subject, a condensation apparatus (60) to condense the subject's breath and produce a condensate, and a collection apparatus (100) having a collection chamber (102) containing means for testing the condensate to determine its chemical properties. The device (10) also include a system for removing or standardizing the volatile substances that may be present with the condensate.

62 Claims, 6 Drawing Sheets

DEVICE AND METHOD FOR MONITORING ASTHMA

CROSS-REFERENCE TO RELATED PROVISIONAL APPLICATION

The present application claims the benefit of the earlier filing date of U.S. Provisional Patent Application Ser. No. 60/112,868, filed Dec. 18, 1998, which is incorporated by reference herein in its entirety.

FIELD OF THE INVENTION

The present invention relates to a device and method for non-invasively monitoring respiratory diseases. More particularly, the present invention relates to a device and method for determining the pH or $NH_4^+$ concentrations of condensed breath exhalate to detect, diagnose and treat asthma.

BACKGROUND OF THE INVENTION

Asthma is a chronic inflammatory disorder of the airways affecting the world population in epidemic proportions. Indeed, approximately five percent of the world population are affected. This means that over 15 million Americans, and hundreds of millions of others worldwide, are susceptible. In the United States, over 400,000 hospitalizations for asthma were required during 1994, and over 1.9 million asthma related emergency room visits were made during 1995. Over 5,000 asthma related deaths occur in the United States each year. See http://www.asthmainamerica.com (Oct. 15, 1999).

In susceptible individuals, asthma causes recurrent episodes of coughing, wheezing, chest tightness, and difficult breathing. Inflammation makes airways sensitive to stimuli such as allergens, chemical irritants, tobacco smoke, cold air and exercise. When exposed to such stimuli, airways may become swollen, constricted, filled with mucus, and hyper responsive to stimuli.

There currently is no cure for asthma, but two types of treatments that suppress asthma symptoms and prevent attacks are currently used by many asthma sufferers. One of these types of treatments employs quick-relief medications, such as inhaled bronchodilator therapy, which works quickly to suppress symptoms by relaxing airway smooth muscle. The other of these types of treatments employs long-term preventive medications, such as inhaled, oral, or intramuscular corticosteroids, and leukotriene antagonists, which can prevent the onset of symptoms and attacks by controlling the underlying inflammation, thereby keeping persistent asthma under control. Unfortunately, many of the preventive medications have undesirable side effects, such as serious as growth limitation in children, osteoporosis, weight gain, and cataracts. As a result, the failure to properly identify the amount of inflammation in the airways, and therefore the appropriate treatment for a subject's asthmatic condition, may significantly adversely impact the subject's health. To date, however, there is no generally accepted manner of readily determining whether a given patient requires treatment, let alone what specific type of treatment should be used.

Conventionally, asthma is diagnosed by examining a number of indicators and qualitatively assessing the observed results. For example, a clinical diagnosis of asthma is often prompted by a combination of symptoms such as episodic breathlessness, wheezing, chest tightness, and coughing. However, these symptoms often occur only nocturnally and therefore are difficult for a doctor to monitor or measure. In addition, recently manifested symptoms alone are neither diagnostic indicators for asthma nor true measures of severity, so doctors must often evaluate a patient's health over long time periods before a diagnosis of asthma may be made with reasonable confidence. Because of the difficulty inherent in diagnosing asthma, doctors must use a patient's response to asthma treatments as a diagnostic tool. For example, the fact that bronchodilator treatment results in the relief of symptoms generally associated with asthma could indicate the presence of asthma. Disadvantageously, such diagnosis methods may result in the unnecessary application of asthma medications which have undesirable side effects. Accordingly, it would be desirable to have a device and method for readily diagnosing asthma before engaging in a course of treatment.

After a physician has covered the difficult ground of determining whether a person suffers from asthma, the physician must go through another process to determine the degree of severity of the asthma in order to prescribe an appropriate course of treatment. As with the diagnosis of asthma generally, there currently is no simple or noninvasive way to measure the degree of inflammation. There also is no objective method for determining when a course of treatment for airway inflammation can be discontinued. Accordingly, it would be desirable to have a device and method for simply, non-invasively and accurately determining the degree or severity of an asthmatic condition, and to what degree, if at all, a chosen course of treatment will be, or has been, effective.

In the past, few devices and methods for diagnosing asthma have been proposed, and those that have been proposed have not met with success. U.S. Pat. No. 5,922,610 to Alving, et al., issued Jul. 13, 1999, discloses a system and method for diagnosing inflammatory respiratory disorders related to abnormal nitric oxide (NO) levels in exhaled breathing air. The approach of the '610 patent includes a mask into which a subject may breathe, filters for removing substances present in the exhaled air that may interfere with NO measurement, and an instrument which receives the uncondensed exhaled air and uses a chemiluminescence technique to measure the NO level of the exhalate. The approach of the '610 patent therefore is very different from that of the present invention, which is drawn to diagnosing and treating respiratory diseases such as asthma by monitoring the acidity or ammonium concentrations of condensed exhalate.

Other devices and methods have been proposed which collect a breath sample for diagnostic purposes, but like the '610 patent, none of these proposals teach or suggest testing a breath sample for acidity or ammonium concentrations to diagnose asthma or other respiratory diseases. For example, European Patent No. 0759169, published Nov. 23, 1995 (published with English translation of claims only), discloses a process and device for collecting expired breath content, which may later be evaluated to determine the condition and metabolic performance of organs such as the lungs and the respiratory system. Among other significant differences between the present invention and the approach of the '169 patent, the latter does not appear to contemplate any specific respiratory disorders, such as asthma, in connection with which the disclosed device and process may be useful, nor does it appear to teach or suggest testing condensed breath exhalate for acidity or ammonium concentrations as an indicator of any respiratory disease. In addition, the '169 patent does not appear to contemplate incorporating a means for testing a condensate in the breath collection device itself, during or immediately following breath condensate collection. Similarly, U.S. Pat. No. 5,081,871 to Glaser, issued Jan. 21, 1992, discloses an apparatus and method for collecting human exhaled breath for later analysis to determine whether the sample contains harmful substances such as volatile solvents, volatile compounds, endogenous compounds, volatile endogenously produced or used compounds, toxic chemicals, organic solvents, and natural air gasses. The '871 patent does not relate to the collection and testing of a breath condensate, nor does it teach or suggest testing exhalate for acidityor ammonium concentrations to diagnose respiratory diseases. In addition, the device and method of the '871 patent are substantially different from those of the present invention.

SUMMARY OF THE INVENTION

The present invention includes a method and device for monitoring a respiratory disease such as asthma in a subject. The method generally includes the steps of collecting condensate from a subject's breath, testing the condensate to determine its acidity level or ammonium concentration, and evaluating the acidity level or ammonium concentration to determine the presence, absence or status of a respiratory disease in the subject. The method may also include, prior to the testing step, standardizing the volatile substances that may be present within the condensate. This may be done by a gas standardizing step or a degassing step. The gas standardizing step may include, for example, introducing atmospheric air to said condensate to standardize the amount of carbon dioxide in solution. The degassing step may include, for example, introducing an inert gas such as argon or helium to said condensate to remove acidifying carbon dioxide. It is contemplated that many respiratory diseases in humans or other vertebrates may be amenable to monitoring in accordance with the present method, including, for example, inflammatory respiratory diseases such as bronchiolitis, cystic fibrosis, smoking induced diseases, tuberculosis and occupational lung diseases. The method is believed to be particularly applicable to diagnosing and treating asthma.

The step of collecting condensate from a subject's breath may include condensing breath that has been exhaled through the subject's mouth, nose, or both. This step may further entail introducing the subject's breath into a condensation apparatus which is capable of condensing the breath, and moving the condensate into a collection apparatus by force of gravity or by mechanical means, such as a pump. Once a breath sample has been received by the condensation apparatus, and preferably after at least a small sample of condensate has been produced by the condensation apparatus, the breath sample may be recirculated through the condensation apparatus until the condensation apparatus has produced a volume of condensate sufficient for the desired testing. In another aspect of the method of the present invention, the collecting step may include, before introducing a breath sample into the condensation apparatus, cooling the condensation apparatus (or one or more parts thereof) in a home freezer or other type of device to cool the condensation apparatus to a temperature lower than that of the condensate to be tested. The temperature to which the condensation apparatus is cooled, depending upon the material limitations of the apparatus, preferably is at least as low as 0° C., and more preferably still at least as low as −40° C. It will be appreciated, however, that the method of the present invention will operate at both higher and lower temperatures.

The step of testing the condensate may include using means for testing the condensate to determine said acidity level or ammonium level. Such means may include, among other things, an electronic or other type of monitor, or a solid, liquid or gaseous reagent introduced to the condensate directly or indirectly. Commonly available reagents include colorimetric pH reagents such as phenylphthalein, bromthymol blue or methyl red. Preferably, the testing step is performed within the collection apparatus using one or more of such methods, or other appropriate methods, eliminating the need to transport the condensate for testing elsewhere.

The step of evaluating said acidity level or ammonium concentration to determine the presence, absence or status of a respiratory disease in the subject may include, for example, evaluating the acidity level or ammonium concentration to diagnose, determine the severity of, determine a course of treatment for, determine the propriety of altering or discontinuing a course of treatment for, or predicting an impending exacerbation of a respiratory disease in a subject.

The device of the present invention, which may be used in performing the method of the present invention, generally includes a mouthpiece apparatus configured to receive breath from a subject, a condensation apparatus configured for operative connection to the mouthpiece apparatus and to condense the subject's breath and produce a condensate, and a collection apparatus configured for operative connection to said condensation apparatus and having a collection chamber containing means for testing the condensate to determine its chemical properties. The device may also incorporate or be used in conjunction with an apparatus to standardize volatile substances within the condensate. The device therefore makes it possible to receive, condense, standardize and evaluate a breath sample from a subject in a single device in order to determine the presence, absence or status of a respiratory disease in the subject. Preferably, each of the mouthpiece apparatus, condensation apparatus, collection apparatus and collection chamber are separable from each other. More preferably still, the collection chamber is removable and disposable such that, once condensate has been collected therein, the chamber may be shipped to a testing facility. A conventional glass or plastic test tube, for example, would be suitable for many applications as such a disposable collection chamber. The condensation apparatus may include removable insulation, such that the insulation may be removed and the condensation apparatus placed in a home freezer or other cooling device prior to use.

The mouthpiece apparatus preferably includes a mouthpiece, which may be formed so that a subject may comfortably exhale from the user's mouth and/or nose into the mouthpiece apparatus. The mouthpiece apparatus preferably also includes a first one-way valve configured to permit air to be drawn into the mouthpiece apparatus by a subject, and a second one-way valve configured to permit air to pass from the mouthpiece to a distal end of the mouthpiece apparatus. A particle or other type of filter may be positioned in the mouthpiece apparatus between the mouthpiece and the distal end of the mouthpiece apparatus.

The condensation apparatus of the device of the present invention preferably comprises an inner tube surrounded by an insulator. In one aspect of the invention, the inner tube has an outer surface, and the condensation apparatus further comprises an outer tube disposed between the inner tube and the insulator. In such a configuration, the inner surface of the outer tube and the outer surface of the inner tube preferably define a heat transfer chamber in which a solid, liquid or gas cooling material may be disposed to help cool or insulate the inner tube through which breath exhalate is to pass.

The collection apparatus may have a connector portion configured to connect the condensation apparatus to the collection chamber. The collection chamber preferably includes a measuring gradient, which may be configured for use as a quick reference to determine the volume of condensate that has been collected in the collection chamber during use of the device. The collection chamber also preferably contains means for testing the condensate to determine the chemical properties of the condensate. As described previously in connection with the method of the present invention, such means may include, among other things, an electronic or other type of monitor, or a solid, liquid or gaseous reagent introduced to the condensate directly or indirectly. For example, the collection chamber may have a reagent chamber therein containing one or more reagents. It could be configured so that condensate collects in the collection chamber, eventually coming into contact with the reagent in the reagent chamber, or so that as condensate is produced, it enters the reagent chamber within the collection chamber. Alternatively, the means for testing said condensate may comprise a retainer configured to hold a material, such as cloth or paper, in which one or more reagents are embedded or otherwise contained. In one aspect of the device of the present invention in which it is configured for determining the acidity level of a subject's condensate, the reagent may be any pH reagent, including colorimeiric pH reagents such as phenylphthalein, bromthymol blue or methyl red. The means for testing may also include an electrode of an electronic monitor, which may optionally be configured to connect to the collection chamber or another part of the device by snaps, screw threads or other attachment means.

The apparatus for standardizing volatile substances within the condensate may comprise a degassing apparatus or a gas standardizing apparatus. The degassing apparatus may include a manual or automatic pump, or a compressed gas container or other apparatus, for drawing or forcing an inert gas through the condensate before or during the measurement of the acidity level, ammonium concentration, or other characteristics of the condensate. The gas standardizing apparatus also may include a pump or compressed gas container or other apparatus for passing atmospheric air through the condensate in a similar manner.

The foregoing and other features, objects and advantages of the present invention will be apparent from the following detailed description, taken in connection with the accompanying figures, the scope of the invention being set forth in the appended claims.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating preferred embodiments of the invention and are not to be construed as limiting the invention. In the drawings.

DETAILED DESCRIPTION OF THE INVENTION

Figure 1:
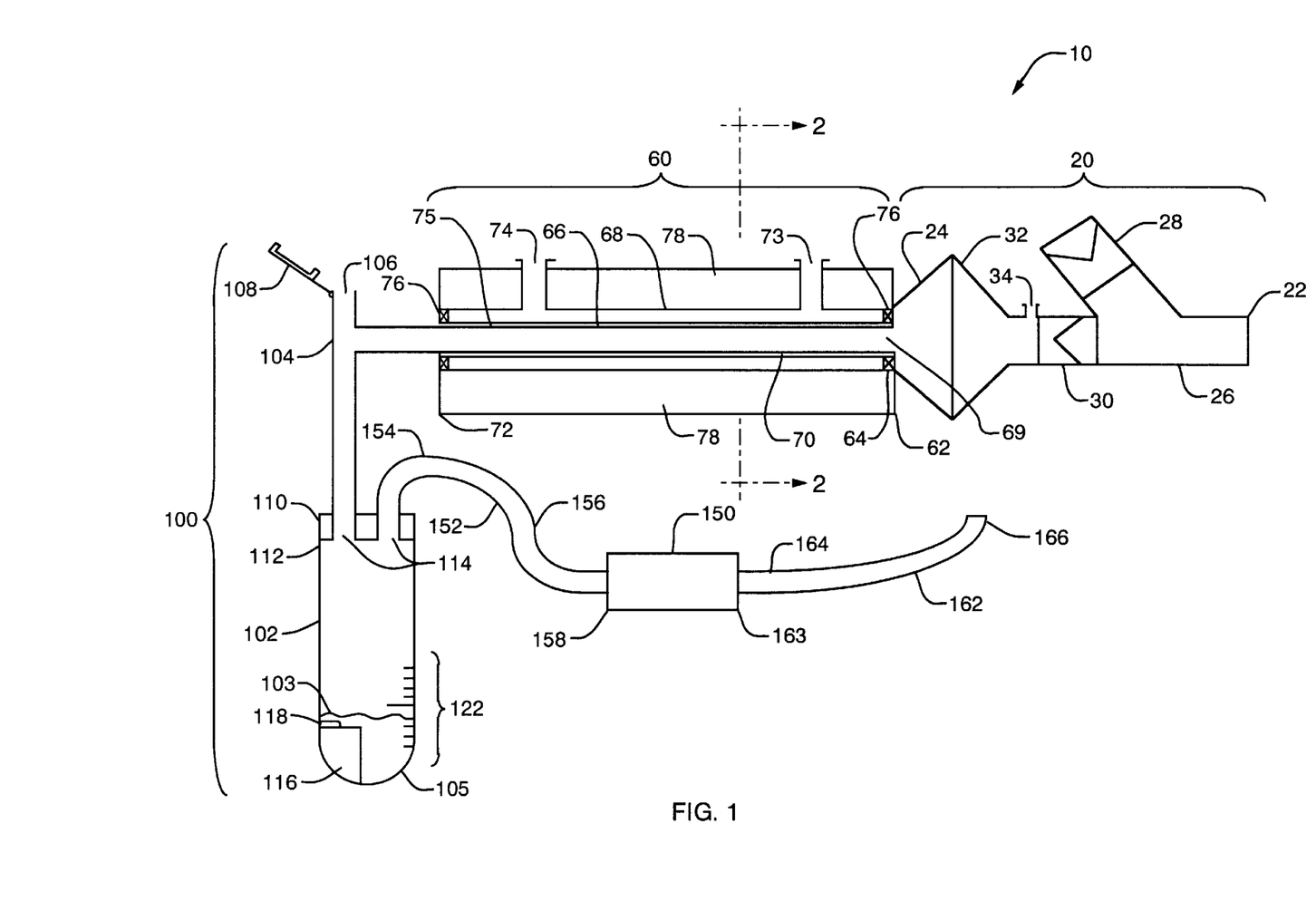
FIG. 1 is a cross-sectional view of one embodiment of the device of the present invention.

Referring now to the drawings, one embodiment of the device of the present invention is illustrated in FIG. 1. As shown in that figure, device 10 of the present invention generally includes a mouthpiece apparatus 20, a condensation apparatus 60, and a collection apparatus 100. Mouthpiece apparatus 20 has a proximal end 22 and a distal end 24, and includes a mouthpiece 26 configured to sealingly engage one or more of a subject's mouth, nose or artificial airway. Although mouthpiece apparatus 20 in FIG. 1 is configured particularly for use with human subjects, the present invention contemplates that it may be configured for use in connection with any other air-breathing beings. In the embodiment of FIG. 1, mouthpiece apparatus 20 also includes a first one-way valve 28, which allows air to be drawn into mouthpiece 26 and into the mouth, nose or artificial airway of an inhaling subject, and a second one-way valve 30, which allows air to exit mouthpiece 26 and enter the remainder of device 10. Mouthpiece apparatus 20 further includes a filter 32 containing a filter element (not shown) which may be selected for eliminating large particles which might originate in the upper airway of a subject, while trapping saliva that could contaminate the exhalate sample. Indeed, the filter element may be selected to have any pore size or electrochemical or other properties so as to gain any desired information regarding condensates derived from different sources within a subject's airway. In FIG. 1, filter 32 is located between second one-way valve 30 and distal end 24 of mouthpiece apparatus 20.

A port 34 may be constructed in mouthpiece apparatus 20 to allow monitoring of airflow, pressure, or other parameters. Mouthpiece apparatus 20 may be constructed from any suitable materials, and is preferably made from commercially available, light-weight plastic and latex components. Preferably, many or all of the components of mouthpiece apparatus 20 are inexpensive, conventional items that are currently commercially available.

At its distal end 24, mouthpiece apparatus 20 attaches to a proximal end 62 of condensation apparatus 60. Preferably, mouthpiece apparatus 20 is configured to be selectively detachable to condensation apparatus 60. Such a design is advantageous because, among other possibilities, filter 32, first and second one-way valves 28 and 30 and other components of mouthpiece 20 may be replaced without replacing condensation apparatus 60, and vice-versa. For similar reasons, it is preferable that the various components of mouthpiece apparatus 20 may be selectively detached from one another. A cap or other valve (not shown) may be used to prevent or regulate communication between filter 32 and condensation apparatus 60.

Condensation apparatus 60 is configured to condense gaseous exhaled breath into a liquid form. In the embodiment of FIG. 1, condensation apparatus 60 includes an inner tube 66 concentrically disposed within an outer tube 68. Inner tube 66 contains a passage 69 extending from a proximal end 64 to a distal end 72 of inner tube 66. Inner tube 66 preferably has a smooth, water repellant inner surface for the easy removal of condensate. The inner diameter of outer tube 68 preferably is larger than the outer diameter of inner tube 66, such that a heat transfer chamber 75 is defined between outer tube 68 and inner tube 66. In the adult model constructed of the embodiment of device 10 of FIG. 1, the length, internal diameter, and wall thickness of inner tube 66 are 12 inches, ⅜ inch, and ¹⁄₁₆ inch, whereas in the child model these dimensions are 12 inches, ¼ inch and ¹⁄₁₆ inch. In the adult model, the length, internal diameter and wall thickness of outer tube 68 are 11 inches, ⅞ inch and ¹⁄₁₆ inch, whereas in the child model these dimensions are 11 inches, ⅞ inch and ¹⁄₁₆ inch. It will be appreciated, however, that these and other dimensions are exemplary only and may be varied to modify the efficiency of condensation apparatus 60.

The materials used to construct inner tube 66 and outer tube 68 are not critical, although they preferably are inexpensive, lightweight and durable. In addition, for reasons that will become apparent, the material used for inner tube 66 preferably is highly heat conductive, whereas the material used for outer tube 68 preferably is highly insulative. In the embodiment of FIG. 1, inner tube 66 is made of finely honed aluminum with a smooth inner surface, and may have a Teflon™ or other water repellent coating. Outer tube 68 is made of a common grade plastic.

A cooling material 70 may be disposed in heat transfer chamber 75 between outer tube 68 and inner tube 66. Cooling material 70 may be a solid, gas or liquid which allows prolonged maintenance of cold temperatures in the condensation apparatus 60. In the embodiment of FIG. 1, for example, cooling material 70 is Coldice Gel Refrigerant™, a high specific heat gel commercially available from Cold ice, Inc. (Oakland, Calif.). In another embodiment, for example, cooling material 70 may be Freon or another chemical. Cooling material 70 also may be a combination of chemicals which, when mixed, produce an endothermic reaction that may be used to cool exhalate moving through tube 66 of condensation apparatus 60 without the need for external cooling. In such a design, condensation apparatus 60 preferably is configured to permit replacement of the chemicals. For example, as shown in FIG. 1, a closeable entry port 73 and exit port 74 may be formed in outer tube 68 for extracting used chemicals and inserting new ones. Although a similar modification may be made to adapt device 10 for the use of an external cooling pump or other such cooling device, there are significant advantages to using an internal cooling system including simplicity and cost.

Outer tube 68 may be designed with integral end caps for retaining cooling material 70 between outer tube 68 and inner tube 66. Alternatively, as shown in FIG. 1, it may be desirable to provide plugs 76 at both ends of outer tube 68 to prevent egress of cooling material 70. Plugs 76 may be composed of rubber, plastic, silicon, metal or any other suitable material. In the embodiment of FIG. 1, for example, plugs 76 are made of a common grade rubber, inserted with plumbing Goop™ made by Eclectic Products, Inc. Cooling material 70 preferably is placed in direct contact with the outer surface of inner tube 66, and does not come into contact with the exhalate moving through tube 66.

Figure 2:
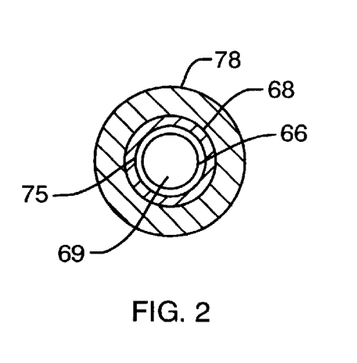
FIG. 2 is a cross-sectional view of the device of FIG. 1 taken along line A—A.

An insulator 78 may be placed around outer tube 68 to extend the effect of cooling material 70 in cooling and condensing exhalate as it passes through condensation apparatus 60. Insulator 78 may be made of materials such as are used commonly in plumbing to insulate pipes, or from other insulating materials. In the embodiment of FIG. 1, insulator 78 is made of foam plastic and has a ⁵⁄₁₆ inch thickness, a 10½ inch length, and a 1½ inch outer diameter. Insulator 78 may be designed to be removable from condensation apparatus 60, such as by sliding over the condensation apparatus 60 longitudinally. Alternatively, insulator 78 may be made with a longitudinal slit to permit it to be easily wrapped around, or removed from, condensation apparatus 60. A cross-sectional view taken at line A—A in FIG. 1 is illustrated in FIG. 2.

Collection apparatus 100 is optionally permanently or detachably connected to a distal end 72 of condensation apparatus 60. Collection apparatus 100 generally comprises a collection chamber 102 configured to collect condensed liquid exhalate (condensate sample 103) from condensation apparatus 60. In the embodiment of FIG. 1, collection apparatus 100 also includes a connector portion 104. Connector portion 104 may be a conventional plastic pipe T-connector having a port 106 to permit venting of any uncondensed exhalate emerging from condensation apparatus 60, or air or other gases emanating from collection chamber 102 as is described in greater detail below. As shown in FIG. 1, port 106 may be selectively blocked by an egress port cap 108. In the embodiment of FIG. 1, the T-connector of connector portion 104 has a ⅜ inch internal diameter. Collection chamber 102 has a top end 112 and a bottom end 105 and is attached to connector portion 104, such as by frictionally engaging a stopper 110 disposed in top end 112 of collection chamber 102, as shown in FIG. 1. Stopper 110 may be a rubber stopper such as those often used with test tubes, or may be made of any other suitable material, and is frictionally disposed in a top end 112 of collection chamber 102. Stopper 110 may have a plurality of passages 114 through it to provide access to collection chamber 102, such as for the insertion of reagents, or testing or medical devices.

Collection chamber 102 may be a conventional plastic or glass test tube, as in the embodiment of FIG. 1, or any other container suitable for collecting condensed exhalate. Preferably, as in device 10, collection chamber 102 is removable and sealable such that a user has the option of collecting condensate in collection chamber 102 and transporting the same to a laboratory for evaluation. Collection chamber 102 may contain one or more solid, liquid or gaseous reagents, disposed either for direct communication with condensate sample 103, or in a separate, rupturable or openable reagent chamber 116. Reagent chamber 116 may be initially sealed and capable of being selectively opened at some point before, during, or after condensate collection to allow direct communication between the reagent and the condensate. The reagent could include any of a variety of dry or liquid substances which, when placed in contact with condensate sample 103, will provide an indication of the relevant chemical properties of the condensate. The decision as to which reagent to include in collection chamber 102 is driven by the chemical properties of interest. When device 10 is to be used for determining the acidity of condensed exhalate, for example, colorimetric pH reagents such as phenylphthalein, bromthymol blue or methyl red may be employed. It is also contemplated that reagent chamber 116 may contain one or more reagents capable of calorimetrically identifying concentrations of ions in condensate sample 103, such as, but not limited to, nitrites and nitrates. One or more additional chambers 116 containing different reagents could also be included, such chambers being individually rupturable or openable for use in multi-step processes comprising a variety of assays.

Figure 3:
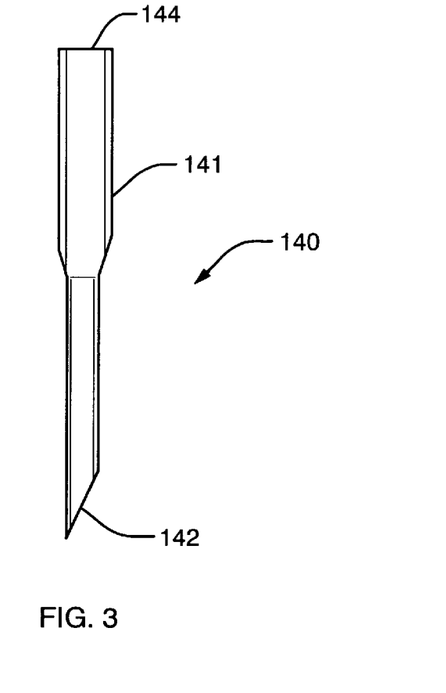
FIG. 3 is a plan view of a pipette which may be used in connection with the device of the present invention.
Figure 4:
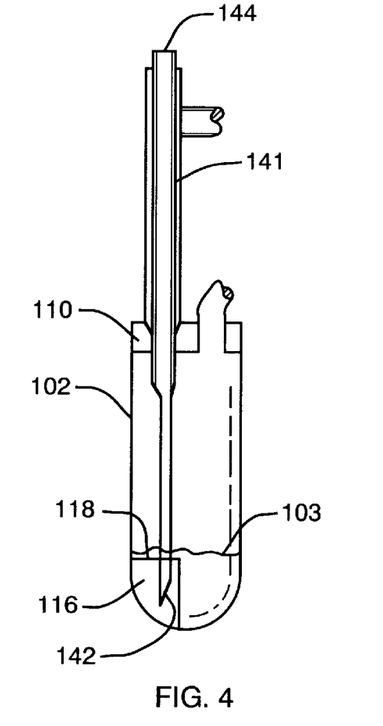
FIG. 4 is a cross-sectional view illustrating the positioning of pipette of FIG. 3 in the collection apparatus of FIG. 1.

In the embodiment of FIG. 1, reagent chamber 116 preferably is sealed but capable of being accessed, for example, by tip 142 of a pipette 140 (FIG. 3). Tip 142 is designed so that, when body portion 141 of pipette 140 is sealingly disposed in one of passages 114 in stopper 110 and has been fully inserted into collection chamber 102, as illustrated in FIG. 4, tip 142 will puncture or otherwise penetrate a top portion 118 of reagent chamber 116. When so disposed, pipette 140 also permits the passage of air (or other gases), whether introduced through first end 144 of pipette 140 or through a passage 114 in stopper 110, through condensate sample 103 and out of collection chamber 102 to atmosphere when pressure is applied, such as by a pressurized gas container, a pump 150, or through other pumping devices such as a syringe, pipette bulb, vacuum or other device, some potential uses of which are discussed in greater detail below. For example, top portion 118 of reagent chamber 116 may be made of a thin gauge plastic or other material which would be readily punctured by a sharp pipette tip 142 made of a material such as surgical steel. As one alternative to the configuration of pipette 140 presented in FIG. 3, first end 144 of pipette 140 may be disposed in close proximity to stopper 110 so that condensate is permitted to continue to travel through connector portion 104 and into condensate sample 103 when pipette 140 is in place.

Figure 5:
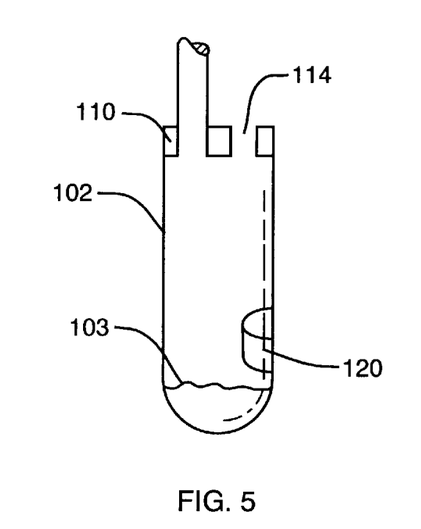
FIG. 5 is a cross-sectional view of the collection chamber of FIG. 1 containing a retainer.
Figure 6:
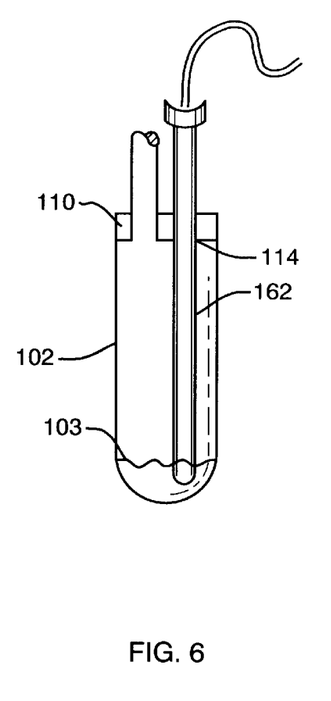
FIG. 6 is a cross sectional view illustrating the positioning of an electrode of an electronic monitor in the collection apparatus of FIG. 1.
Figure 7:
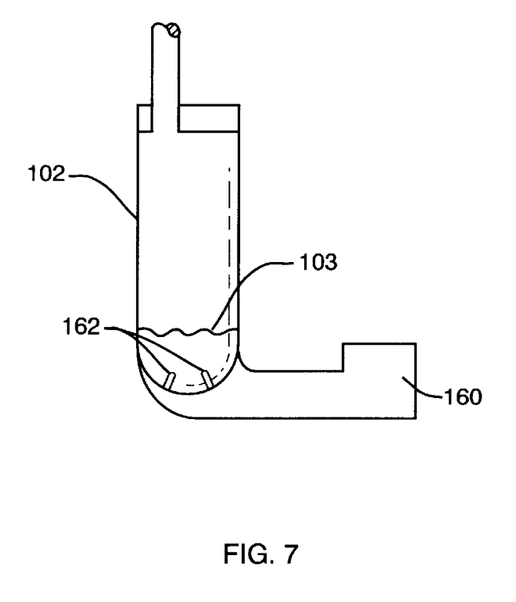
FIG. 7 is a cross sectional view illustrating another use of an electronic monitor in the collection apparatus of FIG. 1.

It will be appreciated that other means for determining properties of condensed exhalate may be employed as an alternative to the use of reagents disposed in a reagent chamber 116. As illustrated in FIG. 5, for example, collection chamber 102 may include a retainer 120 instead of a reagent chamber 116, retainer 120 holding a strip of material (not shown), which could be made of cloth, paper, or another suitable material, and which has a reagent embedded therein or coated thereon. When the level of condensate 103 in collection chamber 102 reaches the material being held by retainer 120, the material may change color to indicate the degree of acidity or other properties of the condensate. As an alternative to the use of a device such as retainer 120 or reagent chamber 116, a user of device 10 could simply dispose the chosen reagent or reagents through a pipette or otherwise through one of passages 114 once a sufficient volume of condensate has been collected for testing in collection chamber 102. As another exemplary alternative, as illustrated in FIG. 6, one of passages 14 may serve as an access site for one or more electrodes 162 of an electronic pH or other ion monitor 160 separate from device 10 and capable of determining selected chemical properties of condensate sample 103. As illustrated in FIG. 6, electrodes 162 may be disposed in collection chamber 102 so that as condensate accumulates, it will contact electrodes 162 of monitor 160. Alternatively, monitor 160 may be attached, by a screwable, snapable or other engagement mechanism, to collection chamber 102 such as in the manner illustrated in FIG. 7, in which electrodes 162 are disposed within collection chamber 102 for contact with condensate sample 103.

Collection chamber 102 preferably includes a measuring gradient 122 which is plainly visible to a user of device 10 so that the volume of collected condensate can be readily determined. Measuring gradient 122 is preferably etched or painted on collection chamber 102, which is preferably made of a transparent material such as clear glass or plastic so that when device 10 is held horizontally, the level of condensate may be viewed against measuring gradient 122.

The use of the device of the present invention will now be described with reference to the embodiment illustrated in FIG. 1, although it will be appreciated that the described method may be readily adapted to many other embodiments of the device. The condensation apparatus 60, preferably without insulator 78, is cooled, to a temperature sufficiently low that condensation apparatus 60 will be capable of condensing exhalate when passed therethrough. Preferably, the temperature to which condensation apparatus 60 is cooled is below 0° C., most preferably −4° C. (the temperature capability of a conventional home freezer), but no lower than −80° C. A conventional home freezer is adequate to accomplish such cooling. Cooling in such a freezer typically requires approximately two hours, and preferably entails the sealing of passage 69 of condensation apparatus 60, at proximal end 62 and distal end 72, so that condensation is not permitted to accumulate therein. When cooling is complete, condensation apparatus 60 is removed from the freezer and insulator 78 is placed over condensation apparatus 60. Mouthpiece apparatus 20 is attached to proximal end 62 of condensation apparatus 60. Connector portion 104 of collection apparatus 100 is attached to distal end 72 of condensation apparatus 60. Port 106 is left open (i.e. with egress port cap 108 not engaging and blocking port 106).

A subject breaths through mouthpiece 26 with regular tidal breathing, or any other manner of breathing which may be desirable, for a sufficient time period for a useful volume of condensate to be collected in collection chamber 102 of collection apparatus 100. Although this time period varies based upon the type of testing means used, it is typically 2 to 10 minutes. During such breathing, device 10 may be tilted so that proximal end 22 of mouthpiece apparatus 20 is at a higher elevation than distal end 72 of condensation apparatus 60. This will allow gravity to assist the subject's breath in moving condensate forming in condensation apparatus 60 into collection apparatus 100. As exhalate is propelled into and through passage 69 in condensation apparatus 60 by the subject's breathing, vapor in the exhalate is condensed and the condensate flows through passage 69 and connector portion 104 and into collection chamber 102. Air in collection chamber 102 is displaced by condensate sample 103 and may pass out of collection chamber 102 through one or more of passages 114 in stopper 110, and through port 106 to atmosphere. Alternatively, egress port cap 108 may be used to block port 106, and one or more passages 114 in stopper 110 opened, such that displaced air may pass out of collection chamber 102 through such one or more passages 114.

Optionally, after a few drops of condensate have been obtained, the circuit formed by condensation apparatus 60 and collection apparatus 100 may be closed and means may be provided for recirculating exhalate through it in order to propel additional condensate through passage 69 and into collection chamber 102. As illustrated in FIG. 1, for example, a first tube 152 may be connected at a first end 154 to a passage 114 in stopper 110, and at a second end 156 to a first end 158 of a pump 150, thus connecting pump 150 to collecting chamber 102. Pump 150 may further be connected at a second end 163 to a first end 164 of a second tube 162, which may be connected at a second end 166 to passage 69 in condensation apparatus 60. With port 106 in connector portion 104 closed by cap 108 and all other ports 14 in stopper 110 closed, the actuation of pump 150 results in the recirculation of the exhalate through passage 69 of condensation apparatus 60, into collection chamber 102, through pump 150 and back through inner tube 66 (or in the reverse direction) repeatedly. Pump 150 is capable of driving condensate from the walls of inner tube 66 and into collection chamber 102. The use of pump 150 therefore augments (or optionally replaces) gravity in the collection of condensate. This makes possible a significant reduction in the time required for sampling (e.g. 2 minutes as opposed to 10 minutes) for the same recovery or condensate. The design or model of pump 150 is not critical, and it may be powered by AC, battery or other suitable power sources.

The device of the present invention may also be used for removing or standardizing the amounts of volatile and other substances within condensate sample 103 for increased measurement accuracy. This may be accomplished by bubbling atmospheric air (i.e. gas standardizing to standardize the amount of carbon dioxide in solution) or an inert gas such as argon or helium (i.e. degassing to remove acidifying carbon dioxide) through the condensate before or during the measurement of the acidity level, ammonium concentration or other characteristics of the condensate. For example, the recirculation means previously described may, alternatively or in addition, be used as a means for removing or standardizing the amounts of volatile and other substances within the condensate. In one embodiment, device 10 may be configured for use with a pumping system such as that previously described comprising pump 150, first tube 152 and second tube 162, but with second end 166 of second tube 162 disconnected from passage 69 in condensation apparatus 60 and permitted to exhaust to the atmosphere, optionally through a filter. A pipette 140 or other such device, open to the atmosphere at a top end 144, may be inserted through one of passages 114 (similar to the manner illustrated in FIG. 4 in connection with inserting a pipette 140 into reagent chamber 116), sealing the same, and pipette tip 142 may extend into the condensate in collection chamber 102. With such a configuration, when pump 150 is activated, ambient air is drawn through pipette 140 and into collection chamber 102, through condensate sample 103, and through first tube 152, pump 150 and second tube 162, after which it is exhausted to atmosphere. The air is drawn through the condensate for a fixed period of time, typically between 1 and 10 minutes (this time period may be greater or lesser depending upon the particular requirements of the properties to be evaluated), thus rapidly equilibrating the condensate sample's carbon dioxide with ambient levels to assist in standardizing measurements.

Alternatively, a self-contained canister of inert or non-reactive gas, such as argon, helium or others, or a reactive gas selected as a reagent, may be connected to top end 144 of pipette 140. Air pump 150 may then be used to draw the gas through condensate sample 103, degassing the sample (i.e. removing volatile substances present in the sample) or allowing the reagent gas to react with the sample as part of a measurement process. In another potential embodiment, pump 150 may be disconnected and the inert or other gas bubbled through the condensate sample as the inert or other gas is emptied from a pressurized cylinder. It should also be noted that where a pipette 140 or other such device is disposed in collection chamber 102 as described, liquid or other reagents may be introduced to the condensate sample 103 through it, or it could be used for drawing condensate sample 103 out of chamber 102 with a syringe, pipette bulb, vacuum device or the like.

The degassing or gas standardizing is particularly valuable in gaining both reproducibility of results by adjusting the carbon dioxide levels in the condensate to a standard level (either zero, or an amount that is in equilibrium with normal air carbon dioxide levels) and an increase in the measurable effect size (larger difference in condensate pH between normals and controls, because of the logarithmic nature of the pH scale). An added benefit of this technique is that it allows retention of the condensate, if desired, for further analysis for chemical content.

Depending upon the configuration of collection chamber 102 and the testing devices incorporated therein, condensate sample 103 may be tested for acidity, ammonium concentration or other properties during or following the collection of the sample. Collection chamber 102 may be provided with a reagent chamber 116 or retainer 120, along with appropriate reagents, for this purpose as previously described. In addition, or as an alternative, however, once an adequate condensate sample has been obtained, collection chamber 102 may be removed from device 10 and sealed for shipment to a laboratory equipped to test condensate sample 103 for acidity level, ammonium concentration or other properties. Thus, collection chamber 102 preferably is disposable, or at least reusable. Of course, condensate sample 103 instead may be withdrawn from collection chamber 102 for shipment or testing, although this may be less cost-effective and cumbersome.

EXAMPLE

We compared the acidity (pH) of deaerated exhaled water from 16 subjects with acute asthma with that from 19 matched controls and 11 subjects who had been treated for acute asthma. We also studied 5 of the 16 subjects with acute asthma longitudinally during systemic glucocorticoid therapy. Patient ages ranged from 8 to 50 years. This study was approved by the Institutional Human Investigation Committee of the University of Virginia Medical Center.

For purposes of the study, asthma was defined as a history of three or more episodes of β-2 agonist reversible airway obstruction, who were admitted to the hospital for dyspnea and demonstrated both tachypnea and an inspiratory/expiratory ratio less than 0.5. We excluded subjects who smoked, had clinical evidence of pneumonia or had a chronic disease other than asthma. Control subjects were recruited from hospital staff and in patients admitted to the hospital for acute, non-respiratory diseases. Additionally, three subjects undergoing direct, undiluted tracheal suctioning were studied, and three subjects were studied before and after three consecutive jet nebulization treatments with albuterol (total of 7.5 mg albuterol in 9 cc of normal saline). The subjects were followed longitudinally with repeated sample collection during and after their hospitalization.

Samples were obtained from the subjects using a device constructed as illustrated in FIG. 1, except as will be noted. The mouthpiece apparatus was a Respirgard II Nebulizer™, manufactured by Marquest Medical Products, Inc. (Englewood, Colo.). The mouthpiece apparatus included a mouthpiece, first and second one-way valves and a 0.3 µm particle filter. The inner tube of the condensation apparatus was a finely honed aluminum tube with a smooth inner surface. The tube had a length of 12 inches, an internal diameter of ⅜ inches, and a wall thickness of ¹⁄₁₆ inches, and was surrounded by a plastic tube (a Xeri-Tube 700™ from Rain-Bird, Inc. of Glendora, Calif.) having a length of 11 inches, an outer diameter of ¾ inches, and a wall thickness of ¹⁄₁₆ inches. Each end of the inner tube protruded approximately ½ inch beyond the ends of the outer tube. The inner and outer tubes were maintained in a axially aligned configuration by two annular silicon plugs, one of which was placed at either end of the outer tube. The inner tube was surrounded by Coldice Gel Refrigerant™, a high specific heat gel commercially available from Cold ice, Inc.

(Oakland, Calif.). The outer tube was surrounded by a tubular insulator made of foam plastic and had a length of 10½ inches, an outer diameter of 1½ inches and a wall thickness of 5/16 inch.

The distal end of the condensation apparatus was connected to a conventional ⅜ inch plastic T-connector obtained from Rain-Bird, Inc. (Glendora, Calif.). One end of the T-portion of the T-connector was open to atmosphere, and the other was frictionally disposed in a plastic test tube. The pH testing apparatus used was a Cardy Twin pH meter (Horiba, Japan) or a Corning pH Micro1 (Corning, N.Y.).

The inner tube of the condensation apparatus was rinsed with distilled water and dried with forced air. The entire condensation apparatus, including the insulator, was placed in a freezer at −40° C. for at least 60 minutes. For each sample taken from each subject, the mouthpiece of the device was placed in the subject's mouth, and the subject performed quiet tidal breathing through the mouth until a volume of condensate sufficient for testing had been collected (e.g., from 20 μl to 1 cc, collection of which typically required from 5 to 10 minutes). The testing of samples using the Corning pH Micro 1 was performed by inserting an electrode through the connector, whereas the testing of samples using the Cardy Twin pH meter was performed by removing a portion of the condensate from the collection chamber and placing it on the sensor of the pH meter. A stable pH was achieved in all cases following degassing with Argon for ten minutes. The degassing was accomplished using a pressurized argon cylinder connected by a flexible plastic tube to a pipette disposed in the condensate within the collection chamber. The gas was released at a rate of 350 mL/min by means of a regulator attached to the gas cylinder. Degassing was stopped after pH measurements showed an absence of drift in pH values, indicating the absence of volatile acids, particularly $CO_2$, in the condensate.

Figure 8:
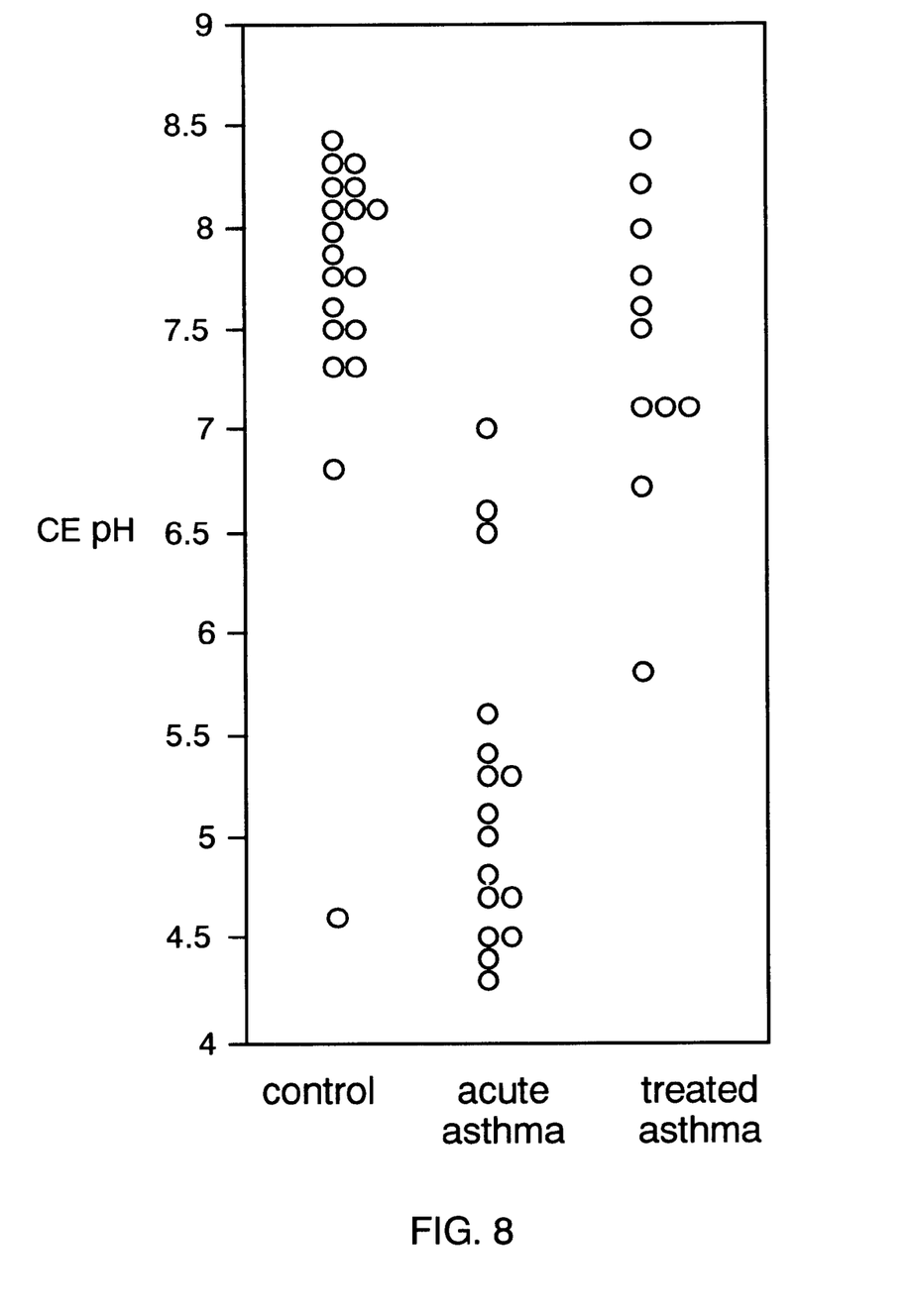
FIG. 8 is a graph showing acidity levels of condensate samples taken for control subjects, subjects suffering from acute asthma, and subjects who had undergone systemic glucocorticoid treatment for acute asthma.
Figure 9:
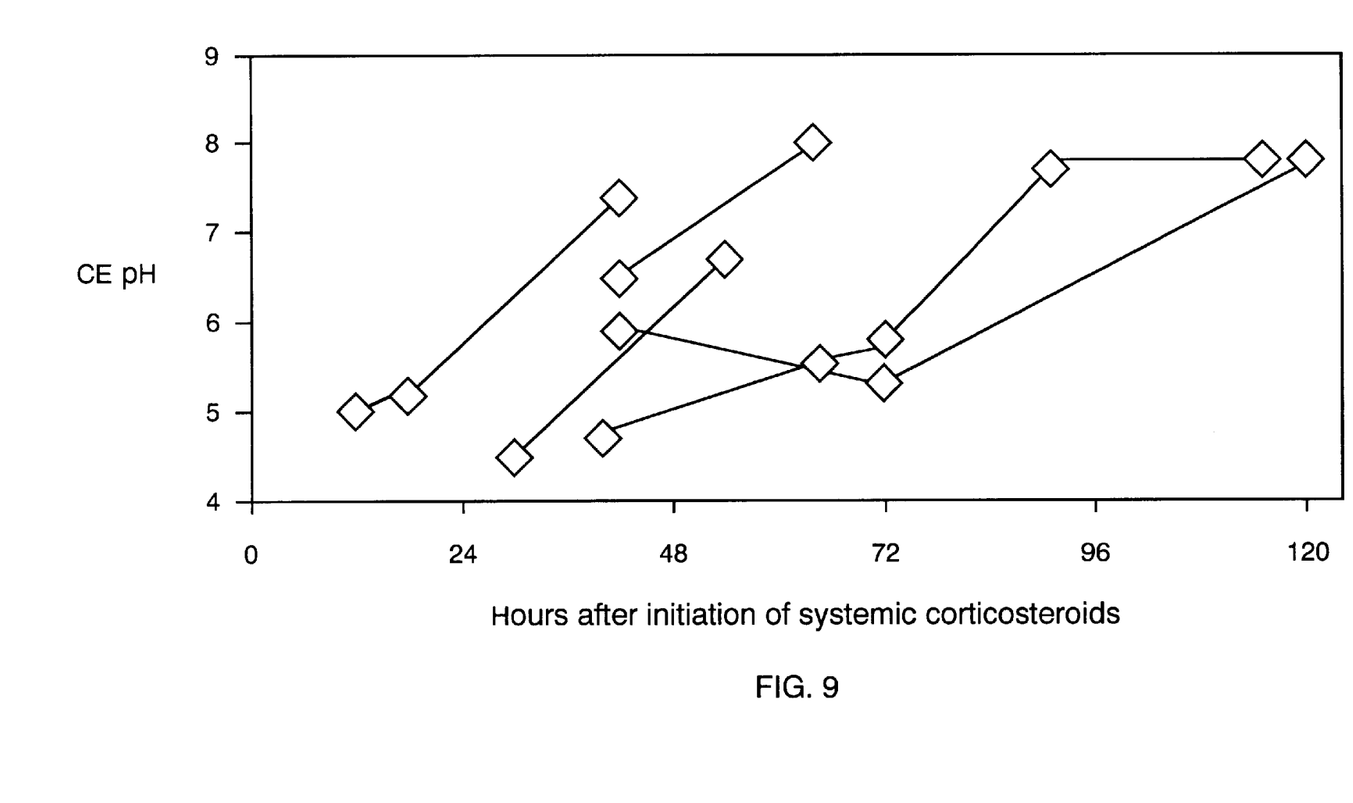
FIG. 9 is a graph showing condensate acidity levels for subjects followed longitudinally during system glucocorticoid treatment.

The results of the samples collected and tested are shown in FIG. 8. The mean pH of specimens from subjects with acute asthma was 5.23±0.21 compared to the mean of the control group of 7.65±0.20 (p<0.001). As can be seen in FIG. 8, the 11 subjects who had received systemic glucocorticoid therapy for longer than 48 hours had higher pH values than acutely ill subjects, in fact approaching normal (7.4±0.23, n=11, p<0.001). Five of the 16 subjects suffering from acute asthma were treated with systemic glucocorticoids (methylprednisolone or prednisone) and followed longitudinally during treatment. As illustrated in FIG. 9, these subjects showed steady increases in pH to normal values during anti-inflammatory therapy. Measurements were highly stable and reproducible (average coefficient of variation=3.3%, 2–16 samples each from six normal subjects and three subjects with acute asthma), unaffected by salivary or therapeutic artifacts, and identical to samples taken directly from the lower airway.

Figure 10:
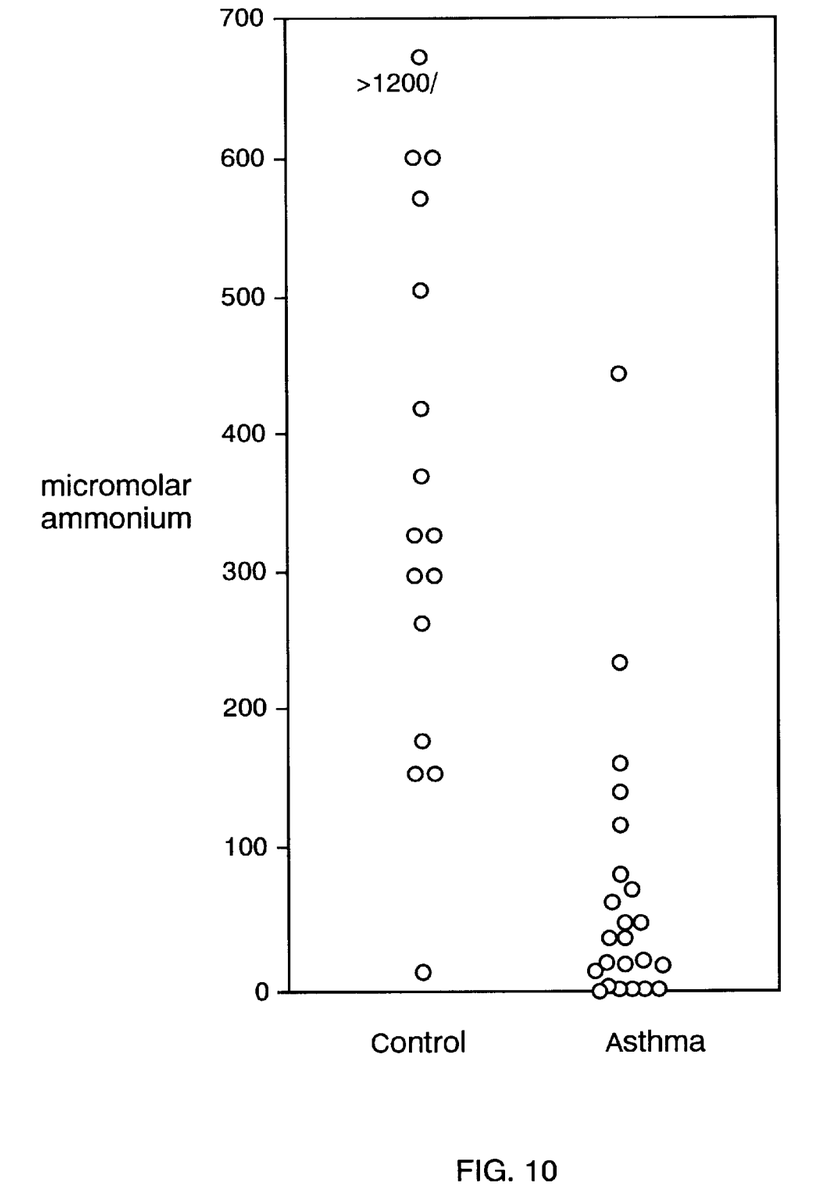
FIG. 10 is a graph showing ammonium concentrations of condensate samples taken for control subjects and subjects suffering from acute asthma.

One potential explanation for the pH disturbance is that, as shown in FIG. 10, ammonium ($NH_4^+$) concentrations were ten-fold lower in asthma than controls. It should be noted that FIG. 10 does not include ammonium data for 3 control subjects, for which samples sufficient for such testing were not available after pH testing, and includes 7 additional acute asthma subjects, with respect to which data was collected as described above. Potential implications of asthmatic airway fluid acidification are diverse, and include enhanced eosinophil-mediated inflammation, dysregulation of airway epithelial function, inhibition of mucociliary clearance, alteration of concentrations and bioactivities of nitrogen oxides including elevations of exhaled nitric oxide. Samples from subjects with asthma—but not from controls—converted airway nitrite to nitric oxide in a pH-dependent manner.

The results of the present tests indicate that: (1) condensed breath from subjects with acute asthma has both pH and $NH_4^+$ concentrations substantially lower than normal; (2) the increased level of acidity appears to be relevant to asthma in that it both accelerates human eosinophil necrosis and causes the conversion of endogenous nitrite ($NO_2^-$) to nitric oxide (NO); (3) the decreased level of ammonium appears, like the increased level of acidity, to be an indicator of the presence and severity of asthma; and (4) breath pH in asthma normalizes with anti-inflammatory therapy. These observations indicate that pH and $NH_4^-$ concentrations are useful for determining the presence, absence or status of asthma, and for treating the disease. In addition, direct comparison revealed that the condensate, deaerated to control for variations in pH ex vivo with exposure to atmosphere, had pH values that were identical to those of specimens suctioned directly from the trachea. This strongly suggests that abnormalities in condensate chemistry, which may be ascertained non-invasively in accordance with the present invention, reflect intrinsic abnormalities of the airway lining fluid, which requires invasive techniques to determine.

As will appreciated in view of the foregoing, the device and method of the invention provide a simple, rapid, non-invasive approach for diagnosing and managing treatment of respiratory disease. The device and method have been shown to provide reproducible results. The device of the present invention provides not only the ability of a user to collect condensate from a subject, but to also test the condensate for chemical properties indicative of asthma (or potentially other diseases) during or immediately following condensate collection. In addition, the device may be configured in detachable parts. This feature not only permits the replacement of parts as required, without replacing the entire device, but also permits the easy cleaning of the condensation apparatus and placement of the condensation apparatus alone in a home freezer, or other cooling device having a limited space, prior to use. In addition, the collection chamber of the collection apparatus may be detached if desired following condensate collection, and shipped to an off-site location for primary or additional testing or analysis. Among other things, these features make the device of the present invention ideal for home use, as well as for use in a clinic, hospital or emergency room setting.

It is believed that the many advantages of the present invention will now be apparent to those skilled in the art. It will also be apparent that a number of variations and modifications may be made thereto without departing from the spirit and scope of the foregoing written description. Accordingly, the foregoing description is to be construed as illustrative only, rather than limiting. The present invention is limited only by the scope of the following claims.

What is claimed is:

1. A method for monitoring a respiratory disease in a subject, said method comprising:

collecting condensate from a subject's breath, said condensate having an acidity level and ammonium concentration;

testing said condensate to determine said acidity level or ammonium concentration; and evaluating said acidity level or ammonium concentration to determine the presence, absence or status of a respiratory disease in the subject.

2. The method of claim 1, wherein said step of evaluating said acidity level or ammonium concentration to determine the presence, absence or status of a respiratory disease in the subject comprises determining the presence, absence or status of an inflammatory respiratory disease.

3. The method of claim 2, wherein said step of determining the presence, absence or status of an inflammatory respiratory disease comprises determining the presence, absence or status of asthma.

4. The method of claim 1, wherein said step of determining the presence, absence or status of an inflammatory respiratory disease comprises determining the presence, absence or status of a respiratory disease that is a member of the group consisting of asthma, bronchiolitis, cystic fibrosis, smoking induced diseases, tuberculosis, and occupational lung diseases.

5. The method of claim 1, wherein said step of determining said acidity level or ammonium concentration of said condensate comprises using means for testing said condensate to determine said acidity level.

6. The method of claim 5, wherein said step of using means for testing said condensate to determine said acidity level or ammonium concentration comprises using an electronic acidity monitor.

7. The method of claim 5, wherein said step of using means for testing said condensate to determine said acidity level or ammonium concentration comprises introducing a reagent to said condensate.

8. The method of claim 7, wherein said step of introducing a reagent to said condensate comprises introducing to said condensate a colorimetric acidity indicator selected from a group consisting of phenylphthalein, bromthymol blue or methyl red.

9. The method of claim 1, wherein said condensate comprises volatile substances, and said method further comprises standardizing said volatile substances within said condensate prior to said testing step.

10. The method of claim 9, wherein said step of standardizing said volatile substances within said condensate comprises a gas standardizing step.

11. The method of claim 10, wherein said gas standardizing step comprises introducing atmospheric air to said condensate.

12. The method of claim 9, wherein said step of standardizing said volatile substances within said condensate comprises a degassing step.

13. The method of claim 12, wherein said degassing step comprises introducing an inert gas to said condensate.

14. The method of claim 13, wherein said step of introducing an inert gas to said condensate comprises introducing argon or helium to said condensate.

15. The method of claim 1, wherein said step of collecting condensate from a subject's breath comprises collecting condensate from a human subject.

16. The method of claim 1, wherein said step of collecting condensate from a subject's breath comprises condensing breath that has been exhaled through the subject's mouth.

17. The method of claim 16, wherein said step of collecting condensate from a subject's breath further comprises condensing breath that has been exhaled through the subject's nose and mouth.

18. The method of claim 1, wherein said step of collecting condensate from a subject's breath comprises:
introducing the subject's breath into a condensation apparatus, said condensation apparatus producing a condensate from said breath; and
moving said condensate into a collection apparatus.

19. The method of claim 18, wherein said step of moving said condensate into a collection apparatus comprises moving said condensate by force of gravity.

20. The method of claim 19, wherein said step of moving said condensate into a collection apparatus comprises moving said condensate using a pump.

21. The method of claim 1, wherein said step of collecting condensate from a subject's breath comprises:
introducing a sample of said breath into a condensation apparatus capable of producing a condensate from said breath; and
collecting in a collection apparatus said condensate produced by said condensation apparatus;
recirculating said breath through said condensation apparatus until said collection apparatus has collected a volume of condensate sufficient for testing.

22. The method of claim 1, wherein said step of collecting condensate from a subject's breath comprises:
providing a condensation apparatus;
cooling said condensation apparatus in a home freezer;
removing said condensation apparatus from said home freezer; and
introducing a sample of said breath into said cooled condensation apparatus.

23. The method of claim 22, wherein said step of cooling said condensation apparatus comprises cooling said condensation apparatus to a temperature at least as low as $0°$ C.

24. The method of claim 23, wherein said step of cooling said condensation apparatus comprises cooling said condensation apparatus to a temperature at least as low as $-40°$ C.

25. The method of claim 1, wherein said step of evaluating said acidity level or ammonium concentration to determine the presence, absence or status of a respiratory disease in the subject comprises evaluating said acidity level or ammonium concentration to diagnose a respiratory disease in the subject.

26. The method of claim 1, wherein said step of evaluating said acidity level or ammonium concentration to determine the presence, absence or status of a respiratory disease in the subject comprises evaluating said acidity level or ammonium concentration to determine the severity of a respiratory disease in the subject.

27. The method of claim 1, wherein said step of evaluating said acidity level or ammonium concentration to determine the presence, absence or status of a respiratory disease in the subject comprises evaluating said acidity level to determine whether a course of treatment for a respiratory disease in the subject should be started, altered or discontinued.

28. The method of claim 1, wherein said step of evaluating said acidity level or ammonium concentration to determine the presence, absence or status of a respiratory disease in the subject comprises evaluating said acidity level to predict an impending exacerbation of a respiratory disease in the subject.

29. A method for monitoring asthma in a subject, comprising:
providing a device comprising a mouthpiece apparatus, a condensation apparatus and a collection apparatus;
receiving a subject's breath in said mouthpiece apparatus;
condensing said breath in said condensation apparatus to form a condensate, said condensate having chemical properties;
collecting said condensate in said collection apparatus;
testing said condensate within said collection apparatus to determine said chemical properties; and
evaluating said chemical properties to determine the presence, absence or status of asthma in the subject.

30. The method of claim 29, wherein said step of testing said condensate within said collection apparatus to determine said chemical properties comprises testing said condensate to determine the acidity level of said condensate.

31. The method of claim 29, wherein said step of testing said condensate within said collection apparatus to determine said chemical properties comprises testing said condensate to determine the ammonium concentration of said condensate.

32. A device for monitoring a respiratory disease in a subject, said device comprising:
a mouthpiece apparatus configured to receive breath from a subject;
a condensation apparatus configured for operative connection to said mouthpiece apparatus, and being further configured to condense the subject's breath and produce a condensate having chemical properties; and
a collection apparatus configured for operative connection to said condensation apparatus, said collection apparatus comprising a collection chamber containing means for testing said condensate to determine said chemical properties, wherein the subject's breath may be received, condensed and evaluated in a single device to determine the presence, absence or status of a respiratory disease in the subject, wherein said means for testing said condensate comprises a reagent disposed within said collection chamber.

33. The device of claim 32, wherein said reagent is a solid reagent.

34. The device of claim 32, wherein said condensate has an acidity level and said reagent is useful for measuring said acidity level of said condensate.

35. The device of claim 34, wherein said reagent comprises a colorimetric acidity indicator selected from a group consisting of phenylphthalein, bromthymol blue or methyl red.

36. The device of claim 32, wherein said condensate has an ammonium concentration and said reagent is useful for measuring said ammonium concentration of said condensate.

37. The device of claim 32, wherein said means for testing said condensate comprises a reagent chamber containing at least one reagent.

38. The device of claim 32, wherein said means for testing said condensate comprises a retainer configured to hold a material, said material comprising a reagent.

39. A device for monitoring a respiratory disease in a subject, said device comprising:
a mouthpiece apparatus configured to receive breath from a subject;
a condensation apparatus configured for operative connection to said mouthpiece apparatus, and being further configured to condense the subject's breath and produce a condensate having chemical properties; and
a collection apparatus configured for operative connection to said condensation apparatus, said collection apparatus comprising a collection chamber containing means for testing said condensate to determine said chemical properties, wherein the subject's breath may be received, condensed and evaluated in a single device to determine the presence, absence or status of a respiratory disease in the subject, wherein said means for testing said condensate comprises an electrode monitor, said electrode monitor at least partially disposed within said condensate.

40. The device of claim 39, wherein said electronic monitor is configured to connect to said collection chamber.

41. The device of claim 32, wherein said collection chamber is detachable and disposable.

42. The device of claim 41, wherein said collection chamber comprises a plastic test tube.

43. The device of claim 32, wherein said collection chamber comprises a measuring gradient.

44. The device of claim 32, wherein said mouthpiece apparatus comprises proximal end, a distal end, and a mouthpiece disposed at said proximal end of said mouthpiece apparatus.

45. The device of claim 44, wherein said mouthpiece apparatus further comprises a first one-way valve configured to permit air to be drawn into said mouthpiece apparatus, and a second one-way valve configured to permit air to pass from said mouthpiece to said distal end of said mouthpiece apparatus.

46. The device of claim 45, wherein said mouthpiece apparatus further comprises a particle filter disposed between said mouthpiece and said distal end of said mouthpiece apparatus.

47. The device of claim 32, wherein said condensation apparatus comprises an inner tube surrounded by an insulator.

48. The device of claim 47, wherein:
said inner tube has an outer surface; and
said condensation apparatus further comprises an outer tube disposed between said inner tube and said insulator, said outer tube having an inner surface, and said inner surface of said outer tube and said outer surface of said inner tube defining a heat transfer chamber.

49. The device of claim 45, wherein said heat transfer chamber contains a cooling material.

50. The device of claim 49, wherein said outer tube has a first port therein providing access to said heat transfer chamber, and a second port therein providing access to said heat transfer chamber, wherein said cooling material may be inserted into said heat transfer chamber through said first port and removed through said second port.

51. The device of claim 48, wherein said inner tube is made of aluminum, said outer tube is made of plastic and said insulator is made of foam plastic.

52. The device of claim 32, wherein said collection apparatus further comprises a connector portion configured to connect said collection chamber to said condensation apparatus.

53. The device of claim 52, wherein said connector portion comprises a T-connector having a first T-portion and a second T-portion, said first T-portion being configured to connect said T-connector to said collection chamber and said second T-portion providing a port to atmosphere, wherein uncondensed breath passing through said condensation apparatus and into said T-connector may vent to atmosphere.

54. The device of claim 53, wherein said device further comprises an apparatus to standardize volatile substances within said condensate.

55. The device of claim 54, wherein said apparatus to standardize volatile substances within said condensate comprises a degassing apparatus.

56. The device of claim 55, wherein said degassing apparatus comprises a pump.

57. The device of claim 56, wherein:
said collection chamber has a top end and a bottom end, said top end having a first port therein, and at least a portion of said condensate being disposed in said bottom end of said collection chamber;
a pipette is disposed in said collection chamber, said pipette having a body portion, a first end and a second end, said first end being disposed in communication with atmosphere through said second port in said T-portion, said second end having a tip portion disposed in said condensate, and said body portion being sealingly engaged with said first port of said top end of said collection chamber; and said top end of said collection chamber has a second port therein, said second port connecting said collection chamber to said pump at a first end of said pump, said pump being open to atmosphere at a second end, wherein said pump may draw air from, or force air through, said port in said second T-portion of said T-connector, through said condensate.

58. The device of claim 54, wherein said apparatus to standardize volatile substances within said condensate comprises a gas standardizing apparatus.

59. The device of claim 58, wherein said gas standardizing apparatus comprises a pressurized gas container.

60. The device of claim 59, wherein:

said collection chamber has a top end and a bottom end, said top end having a first port therein, and at least a portion of said condensate being disposed in said bottom end of said collection chamber;

a pipette is disposed in said collection chamber, said pipette having a body portion, a first end and a second end, said first end being disposed in communication with atmosphere through said second port in said T-portion, said second end having a tip portion disposed in said condensate, and said body portion being sealingly engaged with said top end of said collection chamber has a second port therein, said second port being open to atmosphere, and said pressurized gas container is connected to said collection apparatus in communication with said collection chamber through said first port in said top end of said collection chamber, wherein said pressurized gas container may force a gas through said condensate.

61. The device of claim 60, wherein said gas is an inert gas.

62. The device of claim 61, wherein said gas is argon or helium.

* * * * *